United States Patent [19]

Narayanan et al.

[11] Patent Number: 5,629,261

[45] Date of Patent: May 13, 1997

[54] FREE-FLOWING, NON-DUSTING WATER DISPERSIBLE GRANULES OF A WATER-INSOLUBLE, HYDROPHOBIC AGRICULTURALLY ACTIVE CHEMICAL HAVING LOW FRIABILITY AND SUPERIOR CRUSH STRENGTH

[75] Inventors: Kolazi S. Narayanan, Wayne; Edward Fu, Kinnelon, both of N.J.

[73] Assignee: ISP Investments Inc., Wilmington, Del.

[21] Appl. No.: 512,742

[22] Filed: Aug. 8, 1995

[51] Int. Cl.$^6$ .................................................. A01N 25/14
[52] U.S. Cl. .................. 504/116; 71/DIG. 1; 71/904; 424/409
[58] Field of Search .................. 504/116; 424/409; 71/904, DIG. 1

Primary Examiner—José G. Dees
Assistant Examiner—Brian G. Bembenick
Attorney, Agent, or Firm—Walter Katz; Marilyn J. Maue; Joshua J. Ward

[57] ABSTRACT

A free-flowing, non-dusting water dispersible granule (WDG) of a water-insoluble, hydrophobic agriculturally active chemical having low friability and superior crush strength for delivery to a desired site as a stable, rainfast suspension in water, without foaming.

8 Claims, No Drawings

FREE-FLOWING, NON-DUSTING WATER DISPERSIBLE GRANULES OF A WATER-INSOLUBLE, HYDROPHOBIC AGRICULTURALLY ACTIVE CHEMICAL HAVING LOW FRIABILITY AND SUPERIOR CRUSH STRENGTH

BACKGROUND OF THE INVENTION

1. Field of the Invention

This invention relates to water dispersible granules (WDG) of agriculturally active chemicals, and, more particularly, to free-flowing, non-dusting WDGs of water-insoluble, hydrophobic agriculturally active chemicals, which have low granule friability and superior crush strength, and which form stable, non-foaming suspensions in water, for delivery of such chemicals to a desired site.

2. Description of the Prior Art

WDGs are important delivery vehicles for active agricultural chemicals because, unlike emulsion concentrates, they are organic solvent-free, do not have dusting problems present with wettable powders, and can be transported more economically than suspension concentrates. WDGs are prepared by water-bonding particles of the active component. However, in the absence of a binder additive in the system, the granules will gradually lose cohesiveness as the water content is reduced by evaporation. A useful binder additive, therefore, must provide for effective granular crush strength and low friability, while enabling the granules to form stable suspensions in water during use, without deleterious foaming as a result thereof, and to quickly dissipate its binding action when immersed in water.

Ligninsulfonate has been considered the binder of choice in WDG systems. Polyvinylpyrrolidone, in combination with urea, has been suggested for the same use (Canadian Patent 1,209,363).

However, there is a need for new and improved WDG systems in which a combination of components therein will provide free-flowing, non-dusting granules having low granule friability and superior crush strength, and which will form stable suspensions in water without deleterious foaming. In particular, it is desired to provide for effective delivery of water-insoluble, hydrophobic agriculturally active chemicals to a desired site for application of a rainfast film on the infected plant.

SUMMARY OF THE INVENTION

A wet paste composition for making a free-flowing, non-dusting water dispersible granule (WDG) having low friability and superior crush strength of a water, insoluble, hydrophobic agriculturally active chemical capable of forming a stable, and active rainfast suspension of said chemical in water, without foaming, for delivery to a desired site by effective disintegration of the granules, comprising, by weight:

(a) as active component, a water-insoluble, hydrophobic, agriculturally active chemical, 10–90%, optionally, with a filler at the lower end of said range, (b) as disintegrant, cross-linked polyvinylpyrrolidone, 1–6%, (c) as film-former, a rainfast, water-insoluble polymer, 1–5%, (d) as penetrant, a $C_8$–$C_{18}$ alkyl pyrrolidone, 0.05–10%, (e) as suspending agent, an anionic oil soluble surfactant, 0.2–4%, (f) as fluidizer for a hydrophilic medium, an aromatic petroleum oil, 1–20%, (g) a wetting agent, 1–10%, (h) a dispersant, 1–20%, and, optionally, (i) water, 1–10%.

The WDG is made by extruding and drying the wet paste composition, effectively removing components (f) and (i) from the wet paste composition.

DETAILED DESCRIPTION OF THE INVENTION (a) The agriculturally active chemical in the composition of the invention is a water-insoluble, hydrophobic herbicide, insecticide or fungicide; for example, chlorothalonil, such chemicals ordinarily present difficulties in formulating the chemical in a WDG which is dust-free, of high hardness and low friability/attrition, and of producing a suitable stable dispersion for delivery to a desired site which is biologically effective and rainfast.

(b) The disintegrant component of the WDG formulation of the invention is crosslinked polyvinylpyrrolidine (XL PVP).

(c) The film-forming, rainfast component of the composition of the invention suitably is a water-insoluble polymer preferably a copolymer of (i) a crosslinked or non-crosslinked N-alkenyl lactam homopolymer or copolymer in which the lactam unit of the polymer is represented by the formula $$\begin{array}{c} R \\ \diagdown \\ C=O \\ \diagup \\ N \\ | \\ (CH_2)_n - C - CH \\ \phantom{(CH_2)_n -} R_1 \phantom{-} R_2 \end{array}$$

wherein R is $C_3$ to $C_6$ alkylene optionally substituted with $C_1$ to $C_{20}$ alkyl; $R_1$ and $R_2$ are each independently $C_2$ to $C_{20}$ alkyl or hydrogen and n has a value of from 0 or 2, and mixtures thereof, and (ii) a $C_8$ to $C_{30}$ comonomer selected from the group of an alkenoic acid; an alkenylanhydride, ester, ether, amino ester or amino amide and an alpha mono- or di- olefin.

(d) The penetrant is a $C_8$–$C_{18}$ alkyl pyrrolidone.

(e) The suspending agent herein is an anionic oil soluble surfactant such as calcium dodecyl benzene sulfonate.

(f) The fluidizer for a hydrophilic medium is an aromatic oil.

(g) The wetting agent is a lignin sulfonate, etc.

(h) The dispersant suitably is a naphthalene formaldehyde condensate sulfonate, etc.

A preferred film-forming, rainfast polymer is a copolymer of vinyl pyrrolidone and a $C_4$–$C_{30}$ alkyl alpha olefin, preferably a>$C_8$ alkyl alpha olefin.

2. Preparation of WDG (Granulation Procedure)

(a) The weighed ingredients of the WDG/simulation (a total of 200 g to 1 kg) were mixed in a V-shell blender for 10 min. and transferred to a 24-inch pan granulator set at an angle of 50° and a speed of 13 r/min. Granulation was effected by spraying the ingredients with tap water. After granulation, the sample was dried in an oven at 40° C. for at least 6 hour to reduce the moisture level from 10–15% to under 1.5%. Finally, the sample was sieved to yield a free-flowing, non-dusting product having a particle size between 10 and 40 mesh (0.425 mm to 2.0 mm). The granules also can be made by extrusion followed by drying of the extruded product.

(b) Extrusion is a preferred process (See Examples A through F below.

EXAMPLE A

The following ingredients were mixed dry in a twin (V-) shell blender for 10 minutes and ground through a disc mill/air-milled in a two inch micron-Master jet pulvarizer at a feed rate of 20 g per minute and an air pressure of 100 psi.

| Ingredients | Wt., g | % by Wt. |
|---|---|---|
| Carbaryl, technical grade | 149 | 74.5 |
| Dipotassium hydrogen phosphate (buffer) | 10 | 5.0 |
| Agrimer XL ®, disintegrant | 8 | 4.0 |
| Dispersant 1, Reax ® 45 A | 16 | 8.0 |
| Dispersant 2, Lomar ® D | 12 | 6.0 |
| Wetting agent, Morwet ® EFW | 3 | 1.5 |
| Foamaster soap L ®, defoamer | 2 | 1.0 |
| Total | 200 | 100.0 |

160 g dry milled charge was transferred to a 2 L Hobart planetary mixer bowl. 40 g Agrimax 3H was added to the charge gradually, while the stirrer in the Hobart Mixer bowl was set at speed 2. Agrimax 3H was added over a period of 5–30 minutes. The sample appeared extrudable after the addition of ~38 g Agrimax 3H.

The wet paste (145 g) was loaded into a laboratory extruder (LCI Benchtop granulator, which is a basket type extruder with adjustable speed and interchangeable screens, and sample was extruded without compression, with speed at maximum setting (10) and screen opening at 1 mm. Sample extruded well producing short extrudate without sticking. As the mixing time increased, the wet mass appeared wetter and sticky. Wetter granules were longer and were moderately sticky. The wet granules were dried in a laboratory fluid-bed for 15–30 minutes at 40° C. The dried granules were sieved through 10 and 40 mesh screens. Following fractions were obtained.

Wt. retained on 10 mesh screens=31.2 g
Wt. retained on 40 mesh screens=110.63 g
Wt. retained on Pan=1.36 g
Total wt. recovered=143.19 g
% −10+40 granules=110.63/143.19=77.3%

The granule was evaluated for ease and quality of dispersion and friability. Imhoff cone dispersion index was found to be <0.5, Filtration suspension index was 73%, and friability index was 98%.

EXAMPLE B

Example A was repeated except 2240 g of the dry milled charge was transferred to a 4L Hobart mixer in 4 equal batches of 560 g, using an average of 22.85% Agrimax 3H in the wet mix (i.e., a total of 663.3 g or an average of 165.8 g per batch), instead of 20%. 2800 g wet paste was extruded in 4 batches, all batches of extrudates were combined and dried first in a laboratory fluid-bed for 15–30 minutes at 40° C. Followed by a vacuum oven at 50° C. for 24 hours. The dried granules were sieved through 10 and 40 mesh screens. Following fractions were obtained.

Wt. retained on 10 mesh screens=21.4 g
Wt. retained on 40 mesh screens=2135.1 g
Wt. retained on Pan =91.6 g
Total wt. recovered =2248.1 g
% −10+40 granules=(2135.1/2248.1)100=95%

The granule was evaluated for ease and quality of dispersion and friability. Imhoff cone dispersion index was found to be <0.5, Filtration suspension index was 93.6%, and friability index was 95.3%. The commercial flowable 'Sevin' formulation containing 27% active ingredient showed Imhoff cone dispersion index <0.5, and filtration suspension index 90.1

EXAMPLE C

Example A was repeated except the dry charge was as shown in Table 1 below:

| Ingredients | Wt., g | % by Wt. |
|---|---|---|
| Chlorothalonil, technical grade | 171 | 85.5 |
| Agrimer XL ®, disintegrant | 8 | 4.0 |
| Dispersant 1, Reax ® 45 A | 10 | 5.0 |
| Dispersant 2, Lomar ® D | 6 | 3.0 |
| Wetting agent, Morwet ® EFW | 3 | 1.5 |
| Foamaster soap L ®, defoamer | 2 | 1.0 |
| Total | 200 | 100.0 |

173 g of the dry mix was used to prepare the wet paste using 33 g Agrimax 3H and 3 g water. Performance and compositions summary is shown in the Table.

EXAMPLE D

Example A was repeated except the dry charge was as shown in Table 1 below:

| Ingredients | Wt., g | % by Wt. |
|---|---|---|
| Chlorothalonil, technical grade | 167 | 83.5 |
| Agrimer XL ® (disintegrant) | 8 | 4.0 |
| Dispersant 1, Reax ® 45 A | 10 | 5.0 |
| Dispersant 2, Lomar ® D | 10 | 5.0 |
| Wetting agent, Morwet ® EFW | 3 | 1.5 |
| Foamaster soap L ® defoamer | 2 | 1.0 |
| Total | 200 | 100.0 |

168 g of the dry mix was used to prepare the wet paste using 33 g Agrimax 3H and 2.75 g water. Performance and compositions summary is shown in the Table.

EXAMPLE E

Example A was repeated except the dry charge was as shown in Table 1 below:

| Ingredients | Wt., g | % by Wt. |
|---|---|---|
| Chlorothalonil, technical grade | 163 | 81.5 |
| Agrimer XL ®, disintegrant | 8 | 4.0 |
| Dispersant 1, Reax ® 45 A | 12 | 6.0 |
| Dispersant 2, Lomar ® D | 12 | 6.0 |
| Wetting agent, Morwet ® EFW | 3 | 1.5 |
| Foamaster soap L ®, defoamer | 2 | 1.0 |
| Total | 200 | 100.0 |

169 g of the dry mix was used to prepare the wet paste using 32 g Agrimax 3H and 3 g water. Performance and compositions summary is shown in the Table.

EXAMPLE F

Example A was repeated except the dry charge was as shown in Table 1 below:

| Ingredients | Wt., g | % by Wt. |
|---|---|---|
| Chlorothalonil, technical grade | 159 | 79.5 |
| Agrimer XL ®, disintegrant | 8 | 4.0 |
| Dispersant 1, Reax ® 45 A | 16 | 8.0 |
| Dispersant 2, Lomar ® D | 12 | 6.0 |
| Wetting agent, Morwet ® EFW | 3 | 1.5 |
| Foamaster soap L ® defoamer | 2 | 1.0 |
| Total | 200 | 100.0 |

174 g of the dry mix was used to prepare the wet paste using 33 g Agrimax 3H and 3 g water. Performance and compositions summary is shown in the Table.

TABLE 1

SUMMARY OF EXAMPLES A–F,
PERCENT WEIGHT COMPOSITIONS OF DRY MIXES

| Ex | Active Ingredient, Technical | Dispersant 1 | Dispersant 2 | Wetting Defoamer | Wetting Agent | Disintegrant | Buffer |
|---|---|---|---|---|---|---|---|
| A | Carbaryl 74.5 | Reax 45 A 8% | Lomar D 6% | Foamster 1% | Morwet EFW 1.5% | Agrimer XL 4% | $KH_2PO_4$ 5% |
| B | Carbaryl 74.5 | Reax 45 A 8% | Lomar D 6% | Foamster 1% | Morwet EFW 1.5% | Agrimer XL 4% | $KH_2PO_4$ 5% |
| C | Chlorothalonil 85.5% | Reax 45 A 5% | Lomar D 3.0% | Foamster 1% | Morwet EFW 1.5% | Agrimer XL 4% | |
| D | Chlorothalonil 83.5% | Reax 45 A 5% | Lomar D 3.0% | Foamster 1% | Morwet EFW 1.5% | Agrimer XL 4% | |
| E | Chlorothalonil 81.5% | Reax 45 A 6% | Lomar D 6.0% | Foamster 1% | Morwet EFW 1.5% | Agrimer XL 4% | |
| F | Chlorothalonil 79.5% | Reax 45 A 8% | Lomar D 6.0% | Foamster 1% | Morwet EFW 1.5% | Agrimer XL 4% | |

NOTES:
Reax ® 45 A (Westvaco) is lignosulfonic acid/sodium salt
Lomar ® D is a polymerized naphthalene sulfonate condensate sodium salt
Agrimer ® XL is crosslinked polyvinylpyrrolidone
Morwet ® EFW (Witco) is a wetting agent - Mixed alkyl naphthalene sulfonate condensate, sodium salt of carboxylates.
Foamster ® Soap L (Henkel) a tallow soap
Agrimax ® 3H (ISP) a mixture containing long chain alkyl pyrrolidone, anionic oil soluble dispersing agent, petroleum aromatic distillate and water insoluble alkylated polyvinylpyrrolidone 3. Test Procedures Cone Dispersion—15 g. of sample was dispersed in 800 mL of 342 ppm hard water (hardness equivalent to $CaCO_3$) by stirring with a magnetic stir bar for 2 min. The suspension was poured into a 1 L Imhoff dispersion cone, and allowed to settle for 5 min. The sediment volume was then determined, and a sedimentation index was calculated as follows $$\text{Sed. Index} = \frac{\text{sed. vol. (mL)}}{\text{sample wt. (g)}} \times 100$$

Crush Strength—Granules were sieved to provide a sample in the −10+12 mesh range. Granules were placed on balance and crushed firmly with a spatula. The force registered at breakage was recorded as the crush strength. The median of 15 to 20 measurements was reported.

Filtration Suspension—A quantity of sample containing 1 g of technical was added to 250 mL of 342 ppm hard water in a Fleaker™. After 5 min, the Fleaker™ was inverted 30 times to disperse the sample. Immediately, the suspension was then poured into an Imhoff dispersion cone. After 30 min, the upper 90% of the suspension was removed by aspiration. The remaining sample was vacuum filtered through a No. 3 Whatman filter paper, dried, and weighed to determine residual solids. The percent suspended was calculated as follows:

$$\% \text{ Susp.} = \frac{[\text{sample wt} - (\text{residual wt} - 0.1 \times \text{sample wt})]}{\text{sample wt}} \times 100$$

where the sample wt consists only of insoluble components of the formulation.

Friability—Measurements were carried out on a Vanderkamp® friabilator. 10 g of sample, initially between 10 and 40 mesh in size, was loaded into a Roche drum. 25 PFTE balls of 0.6 cm diameter were also loaded into the drum, which was then attached to the friabilator. The sample was subjected to 400 rotations, where each rotation causes the sample to fall a distance of 15 cm. Afterwards, the sample was sieved through a 40 mesh screen, and the weight of sample remaining above 40 mesh was determined. A friability index was calculated as follows:

$$\text{Friability Index} = \frac{\text{sample wt above 40 mesh}}{\text{total sample wt}} \times 100$$

Foaming—100 mL of 342 ppm hard water and 5 g of sample were added to a 500 mL fleaker. The suspension was shaken vigorously by hand 60 times, and then allowed to settle for 2 min. The suspension was again shaken 60 times, after which the foam height was measured after 10 s and 2 min. The last step was repeated to produce a second set of values at 10 s and 2 min. A foaming index was calculated as follows:

$$\text{Foam Index*} = \frac{(10 \text{ s ht} \times 2 \text{ min ht**})_1 + (10 \text{ s ht} \times 2 \text{ min ht})_2}{20}$$

*Foam Index as defined above is the average of two readings divided by 10.
**in millimeters Wet paste compositions and properties of dry granules are summarized in Table 2 below.

TABLE 2

| | Wet Paste Compositions | | | Properties of Dry Granules | | | |
|---|---|---|---|---|---|---|---|
| Ex. | Dry mix (from Table 1%) % | Water % | Agrimax 3H, % | Cone disp (Sed Index) | Filtr. susp (% Suspended) | Friability (Fri Index) | Crush Strength (Grams) |
| A | 80 | 0 | 20 | <0.5 | 73 | 98 | 30 |
| B | 77.15 | 0 | 22.85 | <0.5 | 93.6 | 95.3 | 25 |
| C | 82.8 | 1.4 | 15.8 | 8.6 | 59 | 98 | 15 |
| D | 82.5 | 1.3 | 16.2 | 4 | 65 | 97 | 18 |
| E | 82.8 | 1.5 | 15.7 | 1 | 70 | 98 | 18 |
| F | 82.9 | 1.4 | 15.7 | 0.7 | 86 | 96 | 12 |

What is claimed is:

1. A wet paste composition for making a free-flowing, non-dusting water dispersible granule having low friability and superior crush strength of a water, insoluble, hydrophobic agriculturally active chemical capable of forming a stable, and active rainfast suspension of said chemical in water, without foaming, for delivery to a desired site by effective disintegration of the granules, comprising, by weight:

(a) as active component, a water-insoluble, hydrophobic, agriculturally active chemical, 10–90%, optionally, with a filler at the lower end of said range, (b) as disintegrant, cross-linked polyvinylpyrrolidone, 1–6%, (c) as film-former, a rainfast, water-insoluble polymer, 1–5%, (d) as penetrant, a $C_8$–$C_{18}$ alkyl pyrrolidone, 0.5–10%, (e) as suspending agent, an anionic oil soluble surfactant, 0.2–4%, (f) as fluidizer for a hydrophilic medium, an aromatic petroleum oil, 1–20%, (g) a wetting agent, 1–10%, (h) a dispersant, 1–20%, and, optionally (i) water, 1–10.

2. A composition according to claim 1 wherein (a) is 70–80%, (b) is 2–4%, (c) is 1.5–5%, (d) is 1–6%, (e) is 0.5–1.5%, (f) is 5–10%, (g) is 2–4.5%, and (h) is 4–16%.

3. A composition according to claim 1 wherein (a) includes a filler.

4. A composition according to claim 1 wherein (c) is N-octylpyrrolidone, (e) is calcium dodecyl benzene sulfonate, (h) is naphthalene formaldehyde condensate sulfonate and (g) is lignin sulfonate.

5. A composition according to claim 1 wherein (c) is a copolymer of vinyl pyrrolidone and a $C_4$–$C_{30}$ alpha olefin.

6. A water dispersible granule which is made by extruding and drying the wet paste composition of claim 1.

7. A water dispersible granule having a cone dispersion of less than 55, a Friability Index of greater than 90, and a crush strength of greater than 10.

8. A water dispersible granule according to claim 6 in which drying removes substantially all of the (f) and (i) components of the wet paste composition of claim 1.

* * * * *